US00PP35115P2

(12) United States Plant Patent
Robinson

(10) Patent No.: US PP35,115 P2
(45) Date of Patent: Apr. 18, 2023

(54) ***MISCANTHUS* PLANT NAMED 'SUNLIT SATIN'**

(50) Latin Name: *Miscanlhus sinensis*
Varietal Denomination: Sunlit Satin

(71) Applicant: Brian Robinson, Kinoulton (GB)

(72) Inventor: Brian Robinson, Kinoulton (GB)

( * ) Notice: Subject to any disclaimer, the term of this patent is extended or adjusted under 35 U.S.C. 154(b) by 0 days.

(21) Appl. No.: 17/747,250

(22) Filed: May 18, 2022

Related U.S. Application Data

(60) Provisional application No. 63/190,777, filed on May 19, 2021.

(51) Int. Cl.
*A01H 5/02* (2018.01)
*A01H 6/46* (2018.01)

(52) U.S. Cl.
USPC ..... Plt./384
CPC ..... *A01H 6/46* (2018.05)

(58) Field of Classification Search
USPC ..... Plt./384
CPC ..... A01H 6/45; A01H 6/46
See application file for complete search history.

(56) References Cited

U.S. PATENT DOCUMENTS

PP14,743 P2 * 5/2004 Speichert ..... A01H 6/46
Plt./384

OTHER PUBLICATIONS

UPOV and CPVO hits to a *Miscanthus* plant named, Sunlit Satin', QZ PBR 2021/0947, filed Mar. 31, 2021.*

* cited by examiner

*Primary Examiner* — Anne Marie Grunberg
(74) *Attorney, Agent, or Firm* — Penny J Aguirre

(57) ABSTRACT

A new cultivar of *Miscanthus sinensis* plant named 'Sunlit Satin' that is characterized by its medium size compact, upright plant habit with a tight base; an average of 1.3 m in height, its upright flower tassels that when opening that have a satiny sheen and are pink in color, its foliage that has a thick central variegated stripe to provide early in the season interest, its flower tassels that turn to copper color later in the season above the maturing foliage, its foliage that has a thick central variegated stripe to provide early in the season interest, and its resilient, wiry foliage with wispy leaf ends that easily follow the direction of the wind.

1 Drawing Sheet

Botanical classification: *Miscanthus sinensis.*
Cultivar designation: 'Sunlit Satin'.

BACKGROUND OF THE INVENTION

The present invention relates to a new and distinct cultivar of *Miscanthus sinensis* and will be referred to hereafter by its cultivar name, 'Sunlit Satin'. 'Sunlit Satin' represents a new cultivar of Japanese silver grass, a cold hardy, perennial ornamental grass grown for landscape use.

'Sunlit Satin' was hand selected by the Inventor as a seedling from an open pollinated parent group of *Miscanthus sinensis* in Kinoulton, Northants, United Kingdom in August of 2016. The parentage is unknown.

Asexual propagation of the new cultivar was first accomplished by division by the Inventor in March 2017 in Kinoulton, Northants, United Kingdom. Asexual propagation by division and tissue culture using meristematic tissue has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Sunlit Satin' as a unique cultivar of *Miscanthus.*

1. 'Sunlit Satin' exhibits a medium size compact, upright plant habit with a tight base;
an average of 1.3 m in height.
2. 'Sunlit Satin' exhibits upright flower tassels that when opening that have a satiny sheen and are pink in color.
3. 'Sunlit Satin' exhibits flower tassels that turn to copper color later in the season above the maturing foliage.
4. 'Sunlit Satin' exhibits foliage that has a thick central variegated stripe to provide early in the season interest.
5. 'Sunlit Satin' exhibits resilient, wiry foliage with wispy leaf ends that easily follow the direction of the wind.

'Sunlit Satin' can be most closely compared to the *Miscanthus sinensis* cultivars 'Gold und Silber' (not patented) and 'Gracillimus' (not patented). 'Gold und Silber' is similar to 'Sunlit Satin' in plant height. 'Gold und Silber' differs from 'Sunlit Satin' in having broader leaves and flower tassels that are dark red in color. 'Gracillimus' is similar to 'Sunlit Satin' in plant height and in having wiry foliage. 'Gracillimus' differs from 'Sunlit Satin' in having a bushier and dense plant habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by RHS Plants, Crocus, Vitro Westland, Provender Nurseries, Waitrose Garden, Genesis Plant Marketing Ltd, Laforet, Plant Providers, Rainbow Plants, and Trawy.

BRIEF DESCRIPTION OF THE DRAWING

The accompanying color photograph illustrates the overall appearance and distinct characteristics of the new *Miscanthus*. The photograph was taken of a plant about 4 years in age as grown outdoors in a field in Kinoulton, Northants, United Kingdom. The photograph provides a side view of a plant of 'Sunlit Satin' and illustrates the habit and color of the inflorescences in fall. The colors in the photograph are as close as possible with the photographic and printing technology utilized and the color values cited in the Detailed Botanical Description accurately describe the colors of the new *Miscanthus*.

DETAILED BOTANICAL DESCRIPTION

The following is a detailed description of 4-year-old plants of the new cultivar as grown outdoors in a field in Kinoulton, Northants, United Kingdom. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms early August through autumn in the United Kingdom.

*Plant type*.—Herbaceous perennial grass.

*Plant habit*.—Clump-forming, compact, upright grass, with slender foliage and a tight base.

*Height and spread*.—Average of 1.3 m in height and 50 to 60 cm in spread as a 4-year-old plant in the landscape.

*Hardiness*.—At least in U.S.D.A. Zones 5 to 9.

*Diseases and pests*.—No susceptibility or resistance to disease or pests has been observed.

*Root description*.—Thin fleshy, primarily NN155D in color, no stolons or rhizomes present.

*Root development*.—An average of 2 weeks for root development in a liner from a division and an average of 4 weeks to produce a young rooted plant.

*Propagation*.—Division and tissue culture.

*Growth rate*.—Vigorous once established.

Culm (stem) description:

*General*.—Rounded, strong.

*Culm aspect*.—Growing from the base, held in an average angle of 5°.

*Culm quantity*.—Average of 50 basal shoots.

*Culm color*.—Young 145C, mature; 150B, mature internodes; 150A to 150B, finely mottled with 157D just below the internode, anthocyanin coloration absent at nodes.

*Culm size*.—Up to 90.3 cm in length, average of 5 mm in diameter.

*Culm internode length*.—10.8 cm.

*Culm surface*.—Moderately glossy, nodes are pubescent with a ring of adpressed short hairs, 1 mm in length, 156D in color.

*Culm pith*.—NN155C in color, 2.5 mm in thickness of straw cross section.

*Culm tillers*.—Not present.

Foliage description:

*Leaf shape*.—Linear.

*Leaf division*.—Simple.

*Leaf base*.—Sheathed, sheath; 21.6 cm in length, 5 mm in width, a blend of 138B and 194A in color.

*Leaf apex*.—Narrow and long acuminate.

*Leaf aspect*.—Moderately carinate, tips twisted, leaves arching.

*Leaf venation*.—Parallel, only main vein is visible, upper side N155A, lower side 144A to 144B.

*Leaf margins*.—Smooth, very sharp when rubbed downwards due to very small sharp teeth.

*Leaf size*.—52 cm in length, 4 mm in width.

*Leaf (blade and sheath) surface*.—Both surfaces glabrous and smooth, upper surface moderately glossy, lower surface matte, no pubescence observed.

*Leaf ligules*.—Moderately pubescent with thin hairs, an average of 1 mm in length, 160D in color.

*Leaf number*.—An average of 9 per culm.

*Leaf arrangement*.—Alternate.

*Leaf color*.—Young upper surface 138A, young and mature lower surface N138B, mature upper surface 137B, leaf flag; 138A, no anthocyanin present on basal leaf sheath.

*Auricles*.—Not observed.

*Flag leaves*.—Frequent.

*Collars*.—Not observed.

*Leaf buds*.—Not observed.

Flower description:

*General description*.—Compact, fan-shaped (trullate) panicle terminating from each stem, composed of numerous slender, silky aggregate cascading racemes of spikelets.

*Lastingness of inflorescence*.—Average of 1 month for spikelets to drop, rest of raceme persistent into winter.

*Fragrance*.—None.

*Panicle size*.—Up to 21 cm in length and 5.3 cm in width.

*Panicle color*.—A blend of 60C, 64C, and N155D.

*Flower number*.—An average of 300 flowers per inflorescence, 600 flowers per plant.

*Flower buds*.—An average of 1.2 cm in length, 2 mm in diameter, narrow ovate in shape, 151B in color, surface is moderately glossy and covered by fine extending hairs from the base of the floret 155C in color.

*Peduncle (rachis)*.—19.8 cm in length and 1.25 mm in width, moderately strong, held in a vertical angle, surface smooth and moderately glossy and 148A, tinged with 185C in color, no hairiness observed on convex surface of apical rachis.

*Pedicels*.—2 mm in length and 0.5 mm in width, moderately strong, held in an average angle of 5°, surface smooth and moderately glossy and 148C in color.

*Spikelet description (flowers)*.—2 flowers per spikelet, an average of 4 mm in height and diameter, 1.2 cm in depth, consisting of 2 glumes, 1 palea, 1 awned lemma, glumes oppositely placed at the base of each individual flower, lemma and palea oppositely placed above the glumes, glumes; an average of 4 mm in length and 0.75 mm in width, very slightly glossy and glabrous surface, ovate in shape, strongly concave, entire margins, cuneate base, narrowly acute apex, no venation visible, color; when opening and fully open glumes 153B, anthocyanin coloration absent, shoulder of lower glume slightly elevated, shape, length, beak, and hairiness of lower glume were not observed, glume bristles; 1 dense whorl of fine callus hairs extending from the base of the floret; 6 mm in length, 158C in color, no anthocyanin observed, lemma; an average of 1.2 cm in length and 0.5 mm in width, slightly glossy and glabrous surface, ovate in shape, strongly concave, entire margins, cuneate base, narrowly acute apex, no venation visible, not fading, color 162C, palea; an average of 4 mm in length and 0.75 mm in width, slightly glossy and glabrous surface, ovate in shape, strongly concave, entire margins, cuneate base, narrowly acute apex, no venation visible, not fading, color 162C, awn; linear in shape, 183C in color.

Reproductive organs:

*Androecium*.—Stamens; average of 2, anthers; narrow oblong in shape, 1.5 mm in length, 0.5 mm in width, 200B in color, filament; 4 mm in length, transparent and 160D in color, pollen; no pollen detected.

*Gynoecium*.—Pistil; 2, 2 mm in length, stigmas; plumose, 1 mm in length, 0.3 mm in diameter, 200A to 200B in color, style; 1 mm in length, 160D in color, ovary; 144A to 144B in color.

*Caryopsis*.—No caryopsis production was observed.

*Fertility*.—Self-incompatible (can only be outcrossed), no apomictis reproduction.

*Coleoptile anthocyanin*.—Not applicable (not seed grown).

*Vernalization*.—Not required.

It is claimed:

1. A new and distinct cultivar of *Miscanthus* plant named 'Sunlit Satin' as herein illustrated and described.

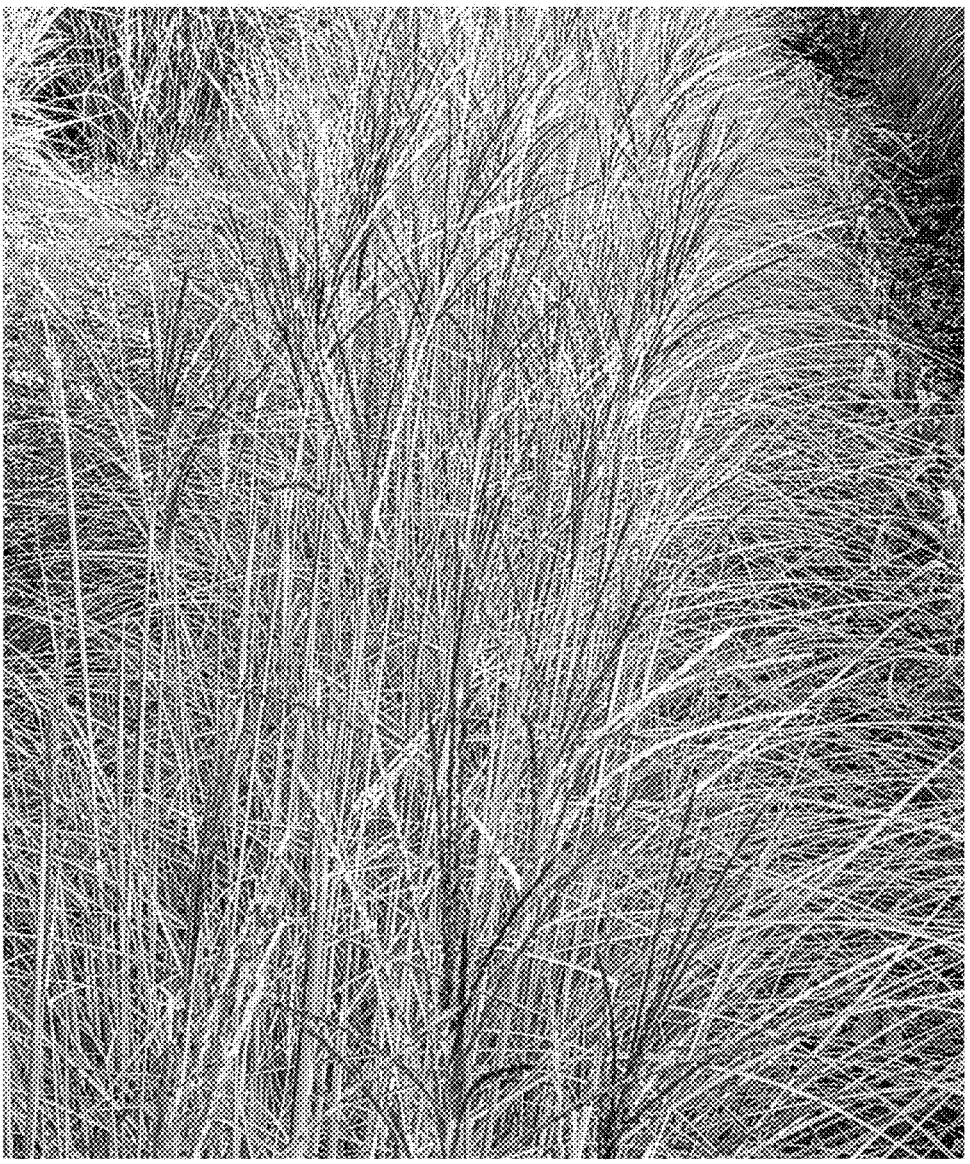

* * * * *